US00PP34880P2

(12) United States Plant Patent
Hardigan et al.

(10) Patent No.: US PP34,880 P2
(45) Date of Patent: Jan. 3, 2023

(54) BLACKBERRY PLANT NAMED 'CELESTIAL'

(50) Latin Name: ***Rubus* subg. *Rubus* Watson**
Varietal Denomination: Celestial

(71) Applicant: The United States of America, as represented by the Secretary of Agriculture, Washington, DC (US)

(72) Inventors: Michael A. Hardigan, Corvallis, OR (US); Chad E. Finn, Corvallis, OR (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 17/697,900

(22) Filed: Mar. 17, 2022

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./203
CPC ... A01H 5/08; A01H 5/00; A01H 6/74; A01H 6/7499
See application file for complete search history.

(56) References Cited

PUBLICATIONS

Research Progress Reports Oregon Raspberry & Blackberry Commision 2019-2020, retrieved from the Internet at https://oregonberries.com/wp-content/uploads/2020/02/2019-20ORBCreports.pdf, 2 intro pages. pp. 14, 41. (Year: 2020).*
Southeast AgNet Radio Network, New Blackberries: Eclipse, Galaxy, and Twilight 2020, retrieved on Apr. 7, 2022 at https://southeastagnet.com/2020/10/21/new-blackberries-eclipse-galaxy-and-twilight/, 4 pp. (Year: 2020).*
Trademark Electronic Search System for Supernova retrieved on Apr. 7, 2022 at https://tmsearch.uspto.gov/bin/showfield?f=doc&state=4805:3nh3vy.2.3, 2 pp. (Year: 2022).*
Upov Explanatory Notes on Variety Denominations under the Upov Convention 2021 UPOV/EXN/DEN/1, retrieved on Apr. 7, 2022 at https://www.upov.int/edocs/expndocs/en/upov_exn_den.pdf, pp. 1-20. (Year: 2021).*
Trademark Electronic Search System (TESS) retrieved on Aug. 3, 2022 at https://tmsearch.uspto.gov/bin/showfield?f=doc&state=4803:z1gxi3.2.3, 2 pp. (Year: 2022).*

* cited by examiner

*Primary Examiner* — June Hwu
(74) *Attorney, Agent, or Firm* — John Fado; Ariel Atkinson

(57) ABSTRACT

A new and distinct blackberry cultivar that originated from seed produced from a cross between the thornless semi-erect maternal blackberry plant 'Eclipse' and the thorny erect paternal blackberry plant ORUS 3681-1, the latter of which introduces genetics from cultivated and wild *Rubus* germplasm from the southeastern U.S. This new blackberry cultivar can be distinguished by its high plant vigor, exceptional yields of small-to-medium sized berries with high gloss, low defects, excellent flavor and fruit quality, and high heat tolerance. The berries are well suited for fresh eating, with good sweetness, aroma, and gloss when picked firm. The new and distinct blackberry variety has fruit that are borne on vigorous canes which contain the 'Merton Thornless' source of genetic thornlessness.

6 Drawing Sheets

Latin name of the genus and species of the plant claimed: 'CELESTIAL' is a blackberry plant that is *Rubus* subg. *Rubus* Watson.

Variety denomination: The new blackberry plant claimed is of the variety denominated 'Celestial' *Rubus* subg. *Rubus* Watson.

BACKGROUND OF THE NEW PLANT

The present invention relates to a new and distinct blackberry cultivar designated 'Celestial' and botanically known as *Rubus* subg. *Rubus* Watson. This new thornless blackberry cultivar was discovered in Corvallis, Oreg. in July 2015, and is the result of a 2012 cross between the maternal blackberry plant 'Eclipse' (U.S. Plant Pat. No. 30,448) and the paternal blackberry plant ORUS 3681-1 (unpatented) and contains $\frac{1}{8}^{th}$ genetics from *Rubus georgicus*. 'Eclipse' was a selection from a cross of the thorny erect blackberry ORUS 1392-1 (unpatented) and thornless semi-erect blackberry 'Triple Crown' (unpatented). ORUS 3681-1 was a selection from a cross of the thornless erect blackberry plant 'Navaho' (U.S. Plant Pat. No. 6,679) and the thorny semi-erect blackberry ORUS 1726-3 (unpatented) and contains $\frac{1}{4}^{th}$ wild genetics from *Rubus georgicus*. 'Celestial' thornlessness is originally derived from 'Merton Thornless' (U.S. Plant Pat. No. 571). The original seedling of the new cultivar was asexually propagated in Benton County, Oreg. The new cultivar was established in vitro from a cane cutting and microcuttings have been taken and rooted from this sort of culture. The cultivar was referred to as "ORUS 4670-1" internally as an experimental designation prior to release. The present invention has been found to be stable and reproduce true to type through successive asexual propagations.

SUMMARY OF THE NEW PLANT

The following are the most outstanding and distinguishing characteristics of this new cultivar when grown under normal horticultural practices in Oregon. The new cultivar is thornless and possesses a semi-erect growth habit. The new cultivar has outstanding plant vigor, the highest among any semi-erect plant so far released by the USDA-ARS-HCRU breeding program in Corvallis, Oreg. and at least as high as 'Chester Thornless' (unpatented). The new cultivar has shown minimal foliar heat stress and low fruit UV damage in years when other semi-erect standards experienced high temperature stress in Oregon, possibly due to the partial wild *R. georgicus* and southeastern blackberry pedigree. The new cultivar ripens 7-14 days earlier than 'Chester Thornless' with similarly high yields of fruit with significantly improved flavor (sweet and aromatic when firm), while ripening at a roughly similar time to 'Triple Crown' with much higher yields. The new cultivar has a long production window for fresh market that extends 2 weeks beyond 'Triple Crown' despite ripening starting at a similar time. The new cultivar produces small-to-medium sized berries that are slightly larger than 'Chester Thornless' berries and smaller than 'Triple Crown', and the berries are firmer and have lower defects than either previous standard. Thus, the new cultivar appears to combine the high plant vigor and exceptional yields of semi-erect varieties like 'Chester Thornless' with the improved eating quality and flavor of more recent, albeit lower yielding semi-erect varieties from the Pacific Northwest such as 'Eclipse', 'Galaxy' (U.S. Plant Pat. No. 30,062) and 'Twilight' (U.S. Plant Pat. No. 30,879), while also introducing some improvements in heat tolerance. No significant disease resistance or susceptibility has been observed in 'Celestial'.

BRIEF DESCRIPTION OF THE PHOTOGRAPHS

This new blackberry plant is illustrated by the accompanying photographs that show the plants, ripening fruit morphology, and harvested fruit; the colors shown are as true as can be reasonably obtained by conventional photographic procedures.

DETAILED DESCRIPTION OF THE NEW CULTIVAR

Figure 1:
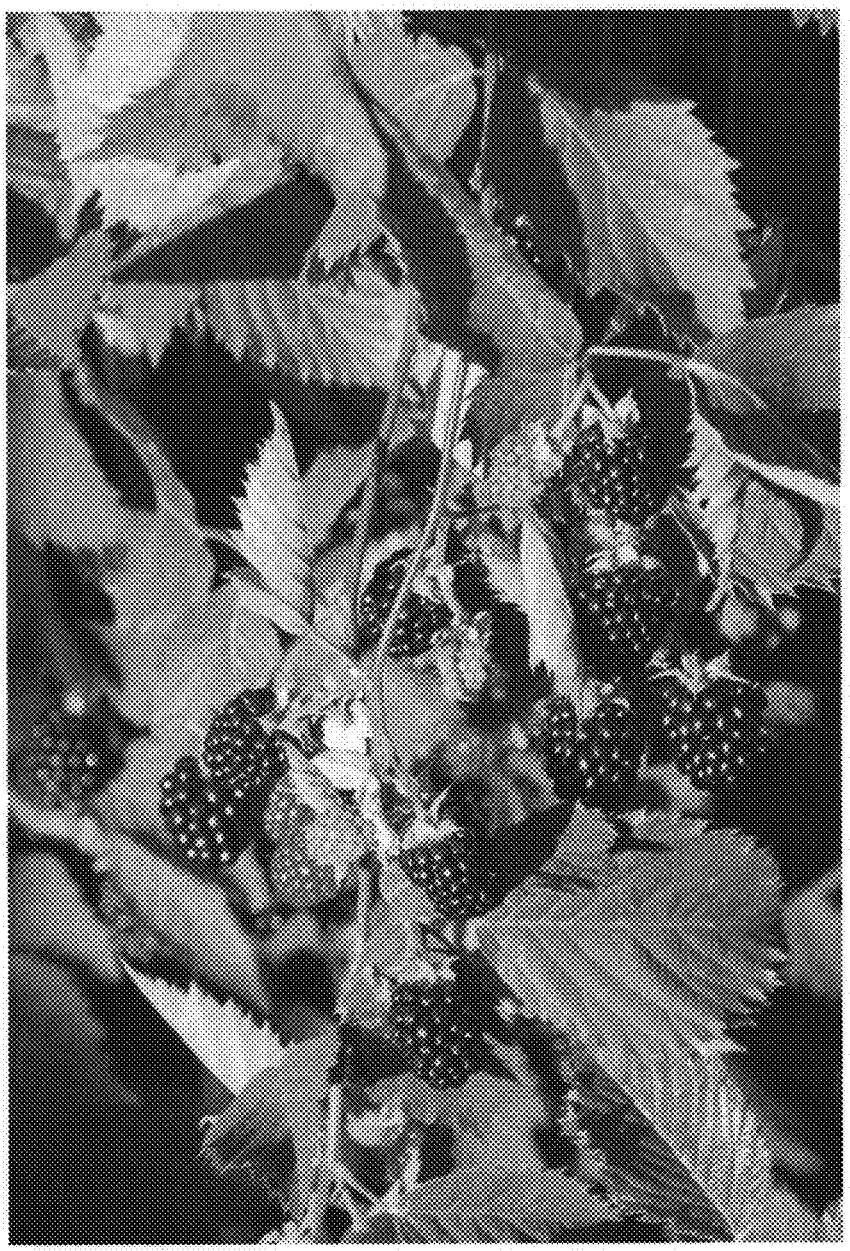
FIG. 1 shows an example of a fruiting cluster with ripe 'Celestial' fruit.
Figure 2:
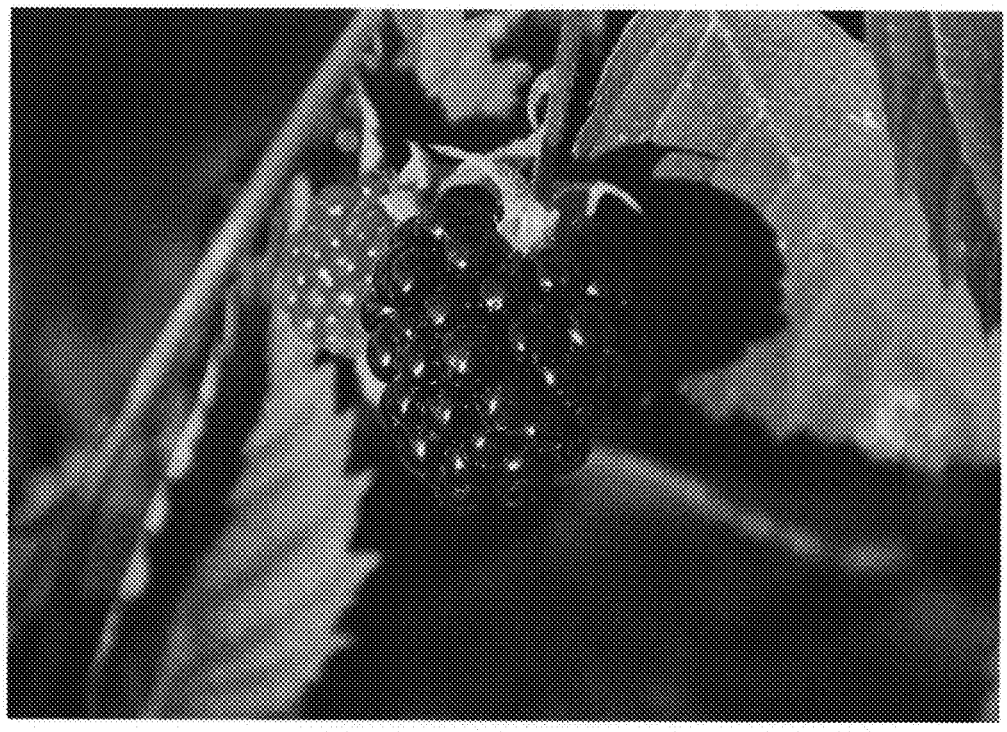
FIG. 2 shows a close-up example of the morphology of 'Celestial' fruit and how it appears on the plant during ripening.
Figure 3:
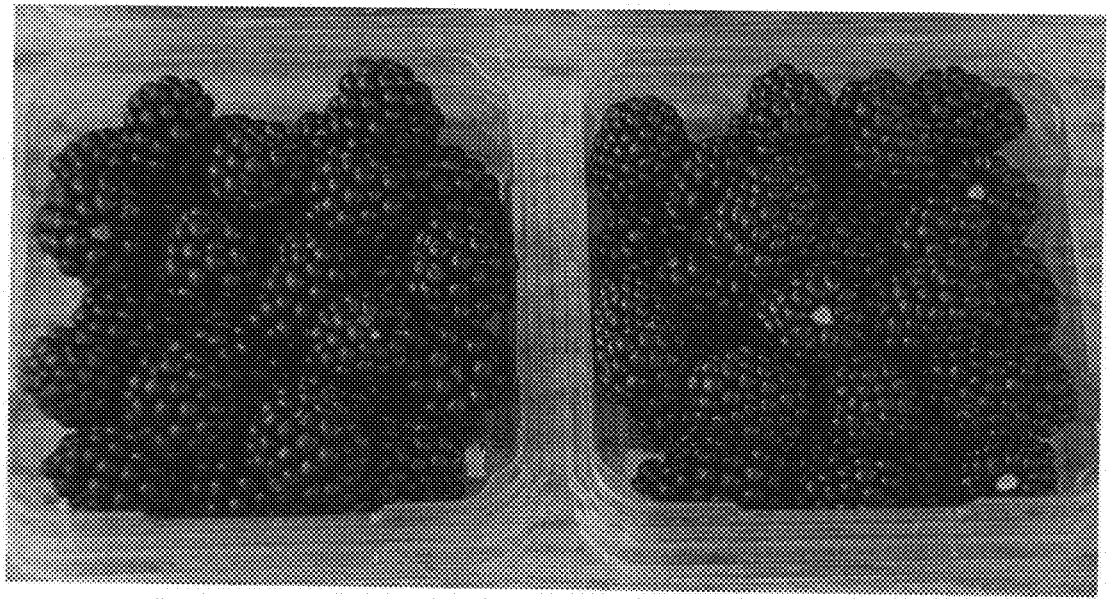
FIG. 3 shows a clamshell of 'Celestial' fruit after 7 days of refrigerated storage at ~4° C. (right) compared to a clamshell of 'Chester Thornless' fruit (left).
Figure 4:
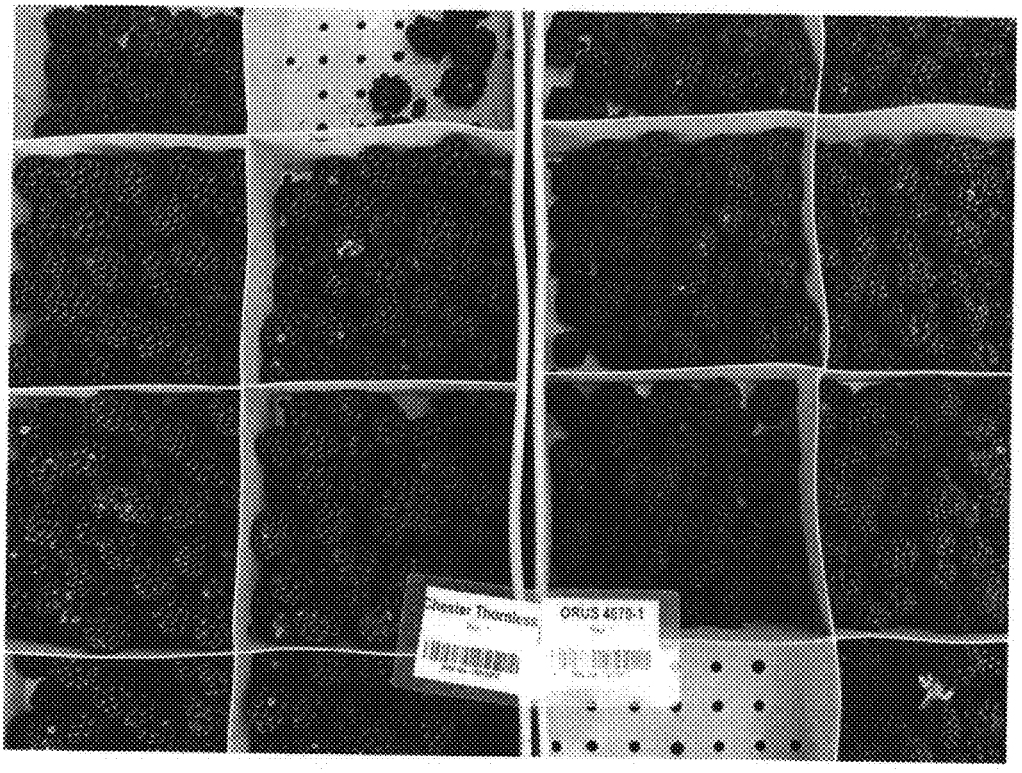
FIG. 4 shows a flat of harvested 'Celestial' fruit (right) compared to a flat of 'Chester Thornless' fruit (left).
Figure 5:
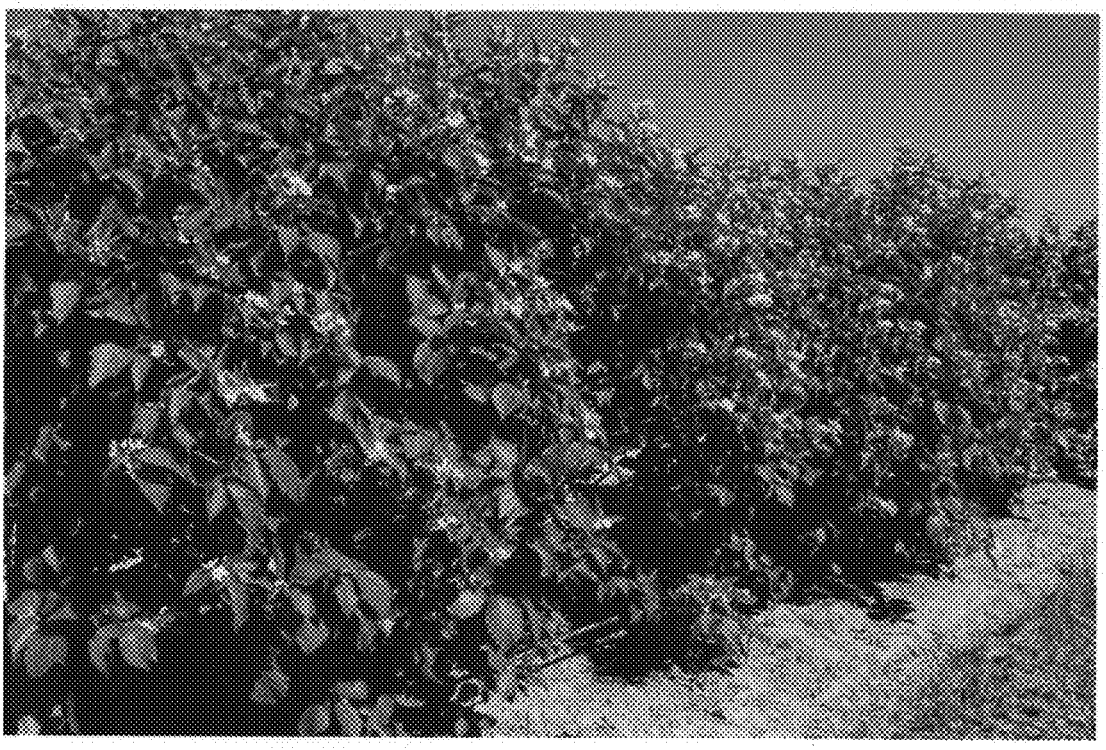
FIG. 5 shows a plot of entire 3 year old 'Celestial' plants during flowering season in early July.
Figure 6:
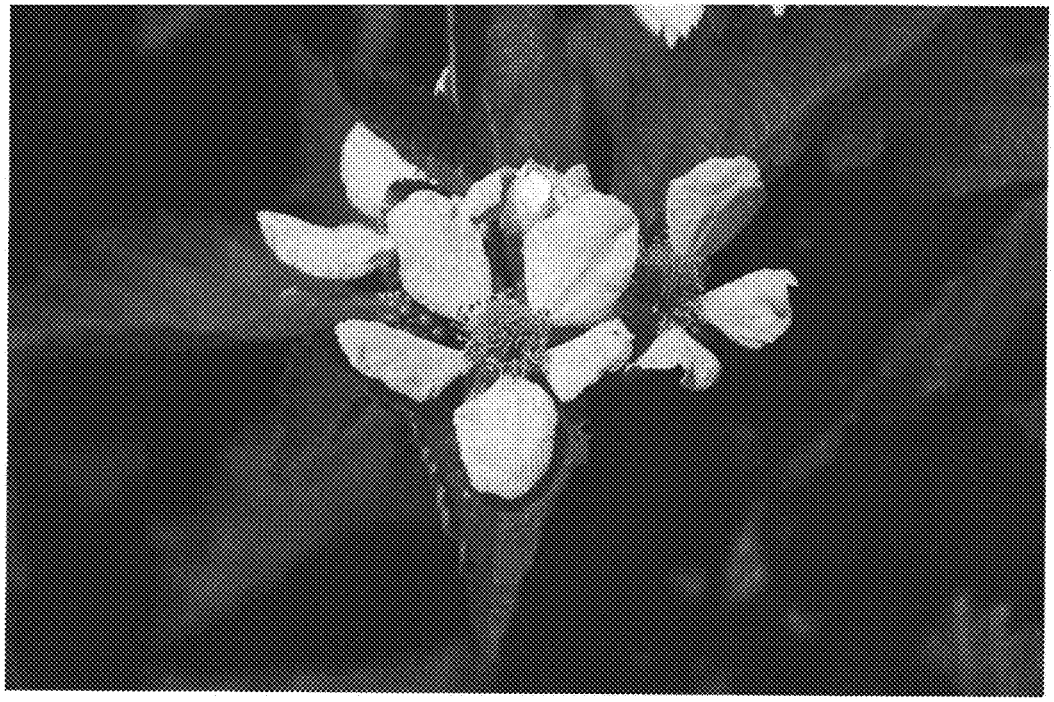
FIG. 6 shows the morphology of a 'Celestial' flower.

The following description of 'Celestial' is based on observations taken from 2016 to 2020 growing seasons in trials in Corvallis and Aurora, Oreg. This description is in accordance with UPOV terminology. Color designations, color descriptions and other phenotypical descriptions may deviate from the stated values and descriptions depending upon variation in environmental, seasonal, climatic, and cultural conditions. 'Celestial' has not been observed under all possible environmental conditions. Color terminology follows The Royal Horticultural Society Colour Chart. London (R.H.S.) ($5^{th}$ edition, 2007).

Table 1 shows plant characteristics of the new cultivar compared with plant characteristics of the blackberry plant 'Twilight'. Characteristics include plant vigor, growth habit, date of bud-break, presence of spines further than 0.6 m from the soil surface, presence of spines less than 0.6 m from the soil surface, weight of primary fruit, uniformity of berry shape, fruit firmness, fruit flavor, fruit soluble solids (%; in Brix), fruit pH, fruit titratable acidity (% as citric acid), and yield (actual kg·plt-1). Fruit measurements are from 2020 trial data collected from OSU-NWREC (Aurora, Oreg.).

TABLE 1

| Characteristic | Celestial | Twilight |
|---|---|---|
| Plant vigor | Very High | High |
| Growth habit | Semi-erect | Semi-erect |
| Date of budbreak | Week 2, March (2022) | Week 1, March (2022) |
| Presence of spines further than 0.6 m from the soil surface | Absent | Absent |
| Presence of spines less than 0.6 m from the soil surface | Absent | Absent |
| Weight of primary fruit | 6.3 g | 8.4 g |
| Uniformity of berry shape | Very good | Excellent |
| Fruit firmness | Very good | Very good |
| Fruit flavor | Very Good | Excellent |
| Fruit soluble solids (%; in Brix) | 13.01 | 14.53 |
| Fruit pH | 3.70 | 3.64 |
| Fruit titratable acidity (% as citric acid) | 10.10 | 10.90 |
| Yield (actual kg · plt-1) | 10.64 | 6.26 |

Table 2 shows floricane and mature primocane characteristics of the new cultivar compared with floricane and mature primocane characteristics of the blackberry plant 'Twilight'. Characteristics include diameter at base, diameter at midpoint, diameter at terminus, internode length at base, internode length at midpoint, internode length at terminus, presence of spines further than 0.6 m from the soil surface, presence of spines less than 0.6 m from the soil surface, floricane color at base, floricane color at midpoint, floricane color at terminus, floricane lateral length, floricane lateral strength, primocane color at base, primocane color at midpoint, primocane color at terminus, and floricane length (range).

TABLE 2

| Characteristic | Celestial | Twilight |
|---|---|---|
| Diameter at base | 1.74 cm | 2.00 cm |
| Diameter at midpoint | 1.27 cm | 1.23 cm |
| Diameter at terminus | 0.37 cm | 0.37 cm |
| Internode length at base | 8.58 cm | 11.93 cm |
| Internode length at midpoint | 8.72 cm | 2.87 cm |
| Internode length at terminus | 4.01 cm | 2.87 cm |
| Presence of spines further than 0.6 m from the soil surface | Absent | Absent |
| Presence of spines less than 0.6 m from the soil surface | Absent | Absent |
| Floricane color at base | RHS 144B | RHS 146A |
| Floricane color at midpoint | RHS 183B | RHS 144A w/ RHS 175A tint |
| Floricane color at terminus | RHS 144A | RHS 144A |
| Floricane lateral length | Medium-long | Medium |
| Floricane lateral strength | Medium | Medium |
| Primocane color at base | RHS N199D + 77A | RHS 144A |
| Primocane color at midpoint | RHS 184A + N144A | RHS 144A w/ RHS 176A streaks |

TABLE 2-continued

| Characteristic | Celestial | Twilight |
|---|---|---|
| Primocane color at terminus | RHS 144A | RHS 144A w/ RHS 185A tint |
| Floricane length (range) | NA (semi-erect mgmt.) | NA (semi-erect mgmt.) |

Table 3 shows primocane foliage characteristics of the new cultivar (no primocane foliage information is available for program semi-erect cultivar standard 'Twilight'). Primocane characteristics include mature compound leaf width, mature compound leaf length, number of leaflets per primocane compound leaf, mature leaflet shape, mature leaflet apex, mature leaflet base, mature terminal leaflet width, mature terminal leaflet length, mature first lateral leaflet width, mature first lateral leaflet length, leaflet margin, leaflet serration teeth length, leaflet serration teeth width at base, spine presence on leaves, pubescence on primocane leaflet: upper surface, pubescence on primocane leaflet: undersurface, primocane leaf color abaxial, primocane leaf color adaxial, petiole length, petiole color: upper surface, petiole color: undersurface, petiolule length: terminal leaflet, petiolule length: first distal leaflet, petiolule color: abaxial, petiolule color: adaxial, stipule length, and stipule width.

TABLE 3

| Characteristic | Celestial |
|---|---|
| Mature compound leaf width | 17.83 cm |
| Mature compound leaf length | 15.35 cm |
| Number of leaflets per primocane compound leaf | Usually 3-5 |
| Mature leaflet shape | Ovate |
| Mature leaflet apex | Broadly acuminate |
| Mature leaflet base | Acute |
| Mature terminal leaflet width | 5.78 cm |
| Mature terminal leaflet length | 8.25 cm |
| Mature first lateral leaflet width | 5.00 cm |
| Mature first lateral leaflet length | 7.68 cm |
| Leaflet margin | Double serrate |
| Leaflet serration teeth length | 0.30 cm |
| Leaflet serration teeth width at base | 0.14 cm |
| Spine presence on leaves | Absent |
| Pubescence on primocane leaflet: upper surface | None |
| Pubescence on primocane leaflet: undersurface | Medium |
| Primocane leaf color abaxial | RHS 147B |
| Primocane leaf color adaxial | RHS 147A |
| Petiole length | 6.27 cm |
| Petiole color: upper surface | RHS 177B |
| Petiole color: undersurface | RHS 177A |
| Petiolule length: terminal leaflet | 3.42 cm |
| Petiolule length: first distal leaflet | 2.37 cm |
| Petiolule color: abaxial | RHS 144D |
| Petiolule color: adaxial | RHS 177A |
| Stipule length | 1.91 cm |
| Stipule width | 0.46 cm |
| Dormant cane average length | 382.5 cm |
| Dormant cane average diameter | 17.33 (base) 12.4 (midpoint) |
| Dormant cane intensity of anthocyanin | Strong |
| Dormant cane number of branches | 8.3 |
| Dormant cane cross section shape | Rounded to angular |

Table 4 shows floricane foliage characteristics of the new cultivar compared with floricane foliage characteristics of the blackberry plant 'Twilight'. Floricane characteristics include mature compound leaf width, mature compound leaf length, number of leaflets per floricane compound leaf, mature leaflet shape, mature leaflet apex, mature leaflet base, mature terminal leaflet width, mature terminal leaflet length, mature first lateral leaflet width, mature first lateral leaflet length, leaflet margin, leaflet serration teeth length, leaflet serration teeth width at base, spine presence on leaves, pubescence on floricane leaflet: upper surface, pubescence on floricane leaflet: undersurface, floricane leaf color abaxial, floricane leaf color adaxial, petiole length, petiole color: upper surface, petiole color: undersurface, petiolule length: terminal leaflet, petiolule length: first distal leaflet, petiolule color: abaxial, petiolule color: adaxial, stipule length, and stipule width.

TABLE 4

| Characteristic | Celestial | Twilight |
|---|---|---|
| Mature compound leaf width | 16.55 cm | 16.65 cm |
| Mature compound leaf length | 14.30 cm | 13.44 cm |
| Number of leaflets per primocane compound leaf | Usually 3-5 | Usually 3 |
| Mature leaflet shape | Ovate | Ovate |
| Mature leaflet apex | Broadly acuminate | Acute |
| Mature leaflet base | Acute | Roundly truncate |
| Mature terminal leaflet width | 6.97 cm | 7.25 cm |
| Mature terminal leaflet length | 9.90 cm | 9.25 cm |
| Mature first lateral leaflet width | 4.83 cm | 6.43 cm |
| Mature first lateral leaflet length | 8.62 cm | 8.52 cm |
| Leaflet margin | Double serrate | Serrated |
| Leaflet serration teeth length | 0.38 cm | 0.33 cm |
| Leaflet serration teeth width at base | 0.25 cm | 0.38 cm |
| Spine presence on leaves | Absent | Absent |
| Pubescence on primocane leaflet: upper surface | None | Light |
| Pubescence on primocane leaflet: undersurface | Medium | Heavy, dense |
| Primocane leaf color abaxial | RHS 147B | RHS 137A |
| Primocane leaf color adaxial | RHS N137A | RHS 138B |
| Petiole length | 4.03 cm | 5.72 cm |
| Petiole color: upper surface | RHS 146 D | RHS 165A |
| Petiole color: undersurface | RHS 146 D | RHS N144D |
| Petiolule length: terminal leaflet | 2.34 cm | 1.52 cm |
| Petiolule length: first distal leaflet | 0.58 cm | 2.11 cm |
| Petiolule color: abaxial | RHS 146 D | RHS 165A |
| Petiolule color: adaxial | RHS 146 D | RHS N144D |
| Stipule length | 1.11 cm | 1.00 cm |
| Stipule width | 0.51 cm | 0.24 cm |

Table 5 shows flower and flowering characteristics of the new cultivar compared with flower and flowering characteristics of the blackberry plant 'Twilight' . Flower and flowering characteristics include date 1st bloom, date full bloom, date last bloom, petal color, number flowers per cluster, number of petals per flower, flower diameter, petal length, petal width, and number of sepals per flower.

TABLE 5

| Characteristic | Celestial | Twilight |
|---|---|---|
| Date 1st bloom | 12-May | 13-May |
| Date full bloom | 20-May | 20-May |
| Date last bloom | 28-June | 30-May |
| Petal color | RHS NN155D | RHS 69C |
| Number flowers per cluster | 12.00 | 8.83 |
| Number of petals per flower | 5.17 | 5.33 |
| Flower diameter | 3.23 cm | 3.24 cm |
| Petal length | 1.55 cm | 1.43 cm |
| Petal width | 1.27 cm | 1.13 cm |
| Number of sepals per flower | 5.00 | 4.83 |
| Peduncle length (cm) | 13.39 | 3.67 |
| Rachis length (cm) | 20.43 | 10.85 |

TABLE 5-continued

| Characteristic | Celestial | Twilight |
|---|---|---|
| Peduncle color | RHS 144A | RHS N144A streaked w/RHS 185A |
| Cyme type | Elongate simple cyme | Elongate simple cyme |

Table 6 shows fruit and fruiting characteristics of the new cultivar compared with fruit and fruiting characteristics of the blackberry plant 'Twilight'. Fruit and fruiting characteristics include date 5% of fruit were ripe, date 50% of fruit were ripe, date 95% of fruit were ripe, weight of primary fruit, weight of secondary fruit, weight of tertiary fruit, diameter of primary fruit at equator, diameter of 2° fruit at equator, diameter of 3° fruit at equator, diameter of 1° fruit at poles: tip, diameter of 1° fruit at poles: base, diameter of 2° fruit at poles: tip, diameter of 2° fruit at poles: base, diameter of 3° fruit at poles: tip, diameter of 3° fruit at poles: base, berry length primary fruit, berry length 2° fruit, berry length 3° fruit, ratio of primary fruit length to width, shape description, uniformity of berry shape, color when full ripe, number of drupelets per fruit, individual seed weight, glossiness, firmness, flavor, texture of fruit when chewed, drupelet skin resistance to abrasion, ease of separation of fruit from pedicel, machine harvestability, resistance to heat damage of fruit, berries per inflorescence—mean, berries per inflorescence range, soluble solids (%; in Brix), pH, titratable acidity (% as citric acid), and yield (actual kg·plt-1). Fruit chemistry data is from 2020 field season at OSU-NWREC.

TABLE 6

| Characteristic | Celestial | Twilight |
|---|---|---|
| Date 5% of fruit were ripe | 20-July | 10-July |
| Date 50% of fruit were ripe | 31-July | 21-July |
| Date 95% of fruit were ripe | 24-August | 9-August |
| Weight of primary fruit | 6.50 g | 8.03 g |
| Weight of secondary fruit | 5.60 g | 5.91 g |
| Weight of tertiary fruit | 5.60 g | 6.00 g |
| Diameter of primary fruit at equator | 2.13 cm | 2.16 cm |
| Diameter of 2° fruit at equator | 1.78 cm | 2.22 cm |
| Diameter of 3° fruit at equator | 1.72 cm | 2.03 cm |
| Diameter of 1° fruit at poles: tip | 1.69 cm | 1.70 cm |
| Diameter of 1° fruit at poles: base | 1.69 cm | 2.18 cm |
| Diameter of 2° fruit at poles: tip | 1.43 cm | 1.70 cm |
| Diameter of 2° fruit at poles: base | 1.52 cm | 2.08 cm |
| Diameter of 3° fruit at poles: tip | 1.44 cm | 1.61 cm |
| Diameter of 3° fruit at poles: base | 1.44 cm | 1.96 cm |
| Berry length primary fruit | 3.00 cm | 2.85 cm |
| Berry length 2° fruit | 2.60 cm | 2.51 cm |
| Berry length 3° fruit | 2.22 cm | 2.47 cm |
| Ratio of primary fruit length to width | 1.3 | 1.32 |
| Shape description | Blunt conical | Blocky |
| Uniformity of berry shape | Medium | Very Consistent |
| Color when full ripe | RHS 203A | RHS 203A |
| Number of drupelets per fruit | 112 | 68.50 |
| Individual seed weight | 2.67 mg | 2.96 mg |
| Glossiness | Medium | Very glossy |
| Firmness | Very firm | Very firm |
| Flavor | Very good | Excellent |
| Texture of fruit when chewed | Very good | Very good |
| Drupelet skin resistance to abrasion | Excellent | Excellent |

TABLE 6-continued

| Characteristic | Celestial | Twilight |
|---|---|---|
| Ease of separation of fruit from pedicel | Easy | Medium |
| Machine haryestability | Good | Good |
| Resistance to heat damage of fruit | Very good | Good |
| Berries per inflorescence - mean | 24.33 | 7.50 |
| Berries per inflorescence range | 12-39 | 7-8 |
| Soluble solids (%; in Brix) | 13.01 | 14.53 |
| pH | 3.70 | 3.64 |
| Titratable acidity (% as citric acid) | 10.10 | 10.90 |
| Yield (actual kg · plt-1) | 10.64 | 6.26 |

COMPARISON WITH PARENTAL AND COMMERCIAL VARIETIES

'Celestial' differs from the female parent blackberry plant 'Eclipse' in that it has a more vigorous plant with greater heat tolerance and significantly greater yields. The fruit are slightly smaller than 'Eclipse', but it produces larger numbers with a higher number of fruits per lateral. The flavor is of similar quality, while the fruit are slightly less glossy, and suffer fewer defects under high temperatures. The fruit have slightly lower sweetness (13.01% Brix) and acidity (10.10% citric acid) compared to 'Eclipse' with slightly higher sweetness (13.38% Brix) and acidity (11.30% citric acid), but still a pleasant sweet and aromatic flavor with low bitter aftertaste.

'Celestial' differs from the male parent blackberry plant ORUS 3681-1 in that it is thornless with a slightly less erect growth habit, and significantly greater yields. The fruit are slightly less glossy than ORUS 3681-1, but have better firmness and flavor, much better shape and uniformity, and lower seediness.

'Celestial' differs from the commercial trailing varieties 'Chester Thornless' and 'Twilight' in that it is 10-14 days earlier ripening than 'Chester Thornless' and begins ripening at a similar time to 'Twilight' but continues for a longer period. 'Celestial' has similar or higher fruit quality after 7 days in refrigerated storage in plastic clam shell packaging at 4° C. to 'Chester Thornless' and similar to 'Twilight'. The 'Celestial' fruit are smaller than 'Twilight' and slightly larger than 'Chester Thornless', with yields that are similar to or better than 'Chester Thornless' and significantly higher than 'Twilight' at the OSU-NWREC in Aurora, Oreg. The fruit flavor is mildly sweet and aromatic, with a flavor slightly less strong than 'Twilight' but much stronger, sweeter, and less tart than 'Chester Thornless'. Both the plant and fruit appear somewhat more resistant to heat-related stress and defects than 'Chester Thornless' and 'Twilight'.

We claim:

1. A new and distinct cultivar of thornless blackberry plant named 'CELESTIAL', substantially as illustrated and described, characterized by its plant vigor, heat tolerance, and exceptional yields of medium sized berries with good fresh eating quality, flavor, gloss, and low defects.

* * * * *